United States Patent [19]
De Bruiju et al.

[11] Patent Number: 6,162,393
[45] Date of Patent: Dec. 19, 2000

[54] CONTACT LENS AND OPHTHALMIC SOLUTIONS

[75] Inventors: Chris De Bruiju, Ahaus, Germany; F. Richard Christ, Laguna Beach, Calif.; Anthony J. Dziabo, Lake Forest, Calif.; Joseph Vigh, Placentia, Calif.

[73] Assignee: NDT, Inc., Laguna Niguel, Calif.

[21] Appl. No.: 09/130,542

[22] Filed: Aug. 6, 1998

[51] Int. Cl.[7] ........................................... A61L 12/14
[52] U.S. Cl. .................. 422/28; 424/405; 424/195.1; 514/839; 514/840
[58] Field of Search ................ 422/28; 514/839, 514/840; 424/405, 195.1

[56] References Cited

U.S. PATENT DOCUMENTS

| | | |
|---|---|---|
| 3,943,251 | 3/1976 | Medow et al. . |
| 4,136,173 | 1/1979 | Pramoda et al. . |
| 4,394,381 | 7/1983 | Sherrill . |
| 4,599,360 | 7/1986 | Fukami et al. . |
| 4,758,595 | 7/1988 | Ogunbiyi et al. . |
| 4,820,352 | 4/1989 | Riedhammer et al. . |
| 4,826,879 | 5/1989 | Yamamoto et al. . |
| 4,836,986 | 6/1989 | Ogunbiyi et al. . |
| 4,894,454 | 1/1990 | Paradies . |
| 4,997,626 | 3/1991 | Dziabo et al. . |
| 5,078,908 | 1/1992 | Ripley et al. . |
| 5,175,161 | 12/1992 | Yokoyama et al. . |
| 5,279,673 | 1/1994 | Dziabo et al. . |
| 5,300,296 | 4/1994 | Holly et al. . |
| 5,306,440 | 4/1994 | Ripley et al. . |
| 5,380,303 | 1/1995 | Holly et al. . |
| 5,547,990 | 8/1996 | Hall et al. . |
| 5,607,681 | 3/1997 | Galley et al. . |
| 5,624,958 | 4/1997 | Isaacs et al. . |
| 5,661,130 | 8/1997 | Meezan et al. . |
| 5,945,446 | 8/1999 | Laub . |

OTHER PUBLICATIONS

Antimicrobial Polymers by John Wiley & Sons, Inc. 1975.

Bausch & Lomb ReNu MultiPlus MultiPrupose Solution, multplus.htm at www.bauseh.com, prior art.

Standard Test Method for Agar Diffusion Cell Culture Screening for Cytotoxicity, American Society for Testing and Materials, ASTM Designation: F 895–84 (Reapproved 1990), pp. 1–4.

Acanthamocha Keratitis—Resistance to Medical Therapy, Linda Ficker, et al, London, 1990, pp. 835–838.

Long–term Antiplaque, Anticalculus, and Antigingivitis Effects of Benzethomium/Polymer Complex in Beagle Dogs, A. Gaffar, et al, J Dent Res Nov. 1981, pp. 1897–1903.

Studies on the Formation of Electrostatic Complexes Between Benzethonium Chloride and Anionic Polymers, Edward A. Tavss, et al, Journal of Pharmaceutical Sciences, 1984, pp. 1148–1152.

*Primary Examiner*—Elizabeth McKane
*Attorney, Agent, or Firm*—Hogan & Hartson, L.L.P.

[57] ABSTRACT

Benzyldimethyl {2-[2-(p-1,1,3,3-tetramethylbutylphenoxy) ethoxy]ethyl} ammonium chloride (BDT) forms the basis of contact lens solutions that are unusually effective at reducing the number and wide variety of pathogenic microorganisms that may infect rigid gas permeable or soft contact lenses. Furthermore, it has been discovered that natural occurring compounds alone and in combination with chemical agents can be used in ophthalmic solutions such as contact lens solution to enhance and complement their anti-microbial, cleaning and wetting activity or to reduce irritation to the eye. The basic contact lens solution comprises an effective concentration of BDT (preferably 1 to 100 parts per million), with naturally occurring plant products possessing activities complementary to BDT, in an isotonic diluent buffered with a physiologically acceptable buffer to a physiologically natural range.

47 Claims, No Drawings

CONTACT LENS AND OPHTHALMIC SOLUTIONS

BACKGROUND OF THE INVENTION

1. Field of the Invention

The present invention relates to contact lens and ophthalmic solutions and in particular relates to methods to disinfect and clean soft and rigid gas permeable (RGP) contact lenses, effectively and safely while maintaining convenience and comfort for the contact lens wearer.

By "effectively" we mean that the levels of specified pathogenic micro-organisms as well as other contaminants such as proteins, lipids, etc., are removed or reduced by a prescribed amount within the period of time contact lenses are kept in their storage case and storage solution. This is commonly taken to be "overnight" which is estimated as 6 hours. By "safely" we mean that the prescribed reduction in pathogen and other contaminant levels is accomplished without concomitant damage to the tissues of the human eye and without deleterious alteration of the contact lens itself. By "convenience" we mean that the contact lens care solution will be such that a minimum number of steps will be required to render the contact lenses clean and disinfected and the complete compliance of the wearer to the prescribed contact lens care procedures will be more likely. By "comfort" we mean that the eyes of the wearer will be able to tolerate the direct instillation of the solution.

2. Description of Related Art

Currently available contact lenses are made of hydrogels causing them to be soft so that they can be comfortably worn. Previously, contact lenses were either hard plastic (PMMA) or RGP and required the contact lens wearing patient to adjust to the uncomfortable sensation of a foreign body in the eye. The advent of soft contact lenses has resulted in an increased adoption of contact lenses by the general population.

Contact lenses are commonly worn on a daily basis and kept in a storage case/solution during the night hours or whenever they are not being worn. During the wear and normal handling of contact lenses, microorganisms as well as biomolecules such as lipids, proteins, etc. can become adhered to the contact lenses and thus transferred to the storage case/solution. Furthermore, a tear film that contains proteins, lipids, and even microorganisms, which represent the natural flora of the ocular surface, covers the surface of the eye. Any of these components found in the tear film or on the external surface of the eye or the surrounding skin can be carried into the storage case/solution on the contact lens.

Some of the microorganisms that may be transferred from the eye or fingers to the storage case/solution may multiply therein and may later be pathogenic to the human cornea or other ocular structures. When the contact lens is returned to the eye following its overnight soaking period, it is possible for these pathogens to be applied to the surface of the eye. Although human tears contain natural anti-microbial agents, a pathogen-bearing lens in contact with the cornea of the eye can serve as a reservoir of infection that might overcome the eye's natural defenses. This is especially the case for soft contact lens as the material tends to uptake the microorganisms. The result of microbial growth—bacterial, protozoan or even fungal—can cause damage to the eye resulting in impaired vision and even blindness. Therefore, contact lenses should be daily disinfected to eliminate pathogenic organisms, usually overnight, i.e., six to eight hours, to protect the wearer's eyes from infection.

As has been stated earlier, it is also possible that other materials of biological origin can be transferred to the contact lens during wear and upon handling and transfer between the eye and the storage case/solution. These materials include cellular debris, proteins, lipids, and inorganic ions such as those of calcium and magnesium. Such materials can adsorb to the surface or become embed in the sub-surface matrix of the soft contact lens often creating persistent deposits that can cause irritation by abrasion against ocular tissues, e.g., cornea and inner surfaces of the eye lids. Furthermore, these deposits can become sufficiently severe to significantly reduce the transparency of the contact lens perhaps leading to impairment of the optical performance of the contact lens. It is therefore of interest to prevent the deposition of or to break up any aggregations of these contaminating molecules during the period of overnight immersion of the contact lenses in the storage case/solution.

Various solutions have been developed over the years to ensure that contact lenses are essentially pathogen and deposit free and can be safely and comfortably worn following overnight storage. These contact lens solutions typically include anti-microbial substances as well as cleaning (active against both lipids and proteins), wetting and other agents for the disinfection and cleaning of contact lenses during storage after wear. These solutions generally have sufficient microbicidal activity that the numbers of potentially pathogenic microorganisms are reduced to a prescribed level during the overnight soaking period.

Disinfection agents typically used for other applications such as hard surface disinfection, instrument disinfection, topical skin disinfection, etc. are not necessarily applicable to contact lens and ophthalmic solutions. The high concentration used and aggressive nature of many of these agents are unsuitable for use with contact lenses due to interaction or damage to the lens or irritation to ocular tissue. "Strong" disinfecting agents are compounds such as thimerasol, chlorhexidine, hydrogen peroxide, and benzalkonium chloride. For example, three (3%) percent hydrogen peroxide instilled directly in the eye or a lens soaked in hydrogen peroxide and applied to the eye will result in pain and severe irritation.

In the case of hydrogen peroxide, prior art answers to the problem of irritation are disclosed in U.S. Pat. Nos. 3,912,451, 4,585,488, 5,145,644 and 5,7666,931. These references show various methods and chemistries wherein the disinfecting period is followed by a neutralizing step using catalase, an enzyme that catalyzes the breakdown of hydrogen peroxide to water. This approach has found some level of acceptance among contact lens wearers. However, acceptance has remained limited, because of the multiple steps of disinfection, neutralization, and rinsing are not convenient to the wearer. More importantly, the potential exists for the neutralization and rinsing steps to be completed incorrectly (non-compliance) leading to the potential for some residual hydrogen peroxide to come in contact with the surface of the eye with the onset of severe stinging and irritation.

More recently, so-called multipurpose solutions (MPS) with chemical disinfection agents, as disclosed in U.S. Pat. Nos. 4,407,791, 4,525,346, 4,758,595, 4,820,352, 4,836,956, 5,422,073, 5,560,186, 5,593,637, and 5,756,045, have largely supplanted hydrogen peroxide systems in the marketplace because they are far more convenient than the hydrogen peroxide systems. In this case the wearer need only purchase and use a single solution leading to advantages in cost and convenience. The challenge of disinfection and cleaning without harm to the eye or the lens is particularly acute with the MPS products, however, since all of the various activities, e.g., wetting, contaminant dispersion, and disinfection, are required to co-exist in a single solution without antagonistic effects of one component on the activity of another. Furthermore, because the MPS can be instilled directly into the eye, the active anti-microbial component of these solutions must provide the required degree of pathogen reduction while being free of irritating or damaging sequelae to the surface and the anterior segment of the eye or to the contact lens itself. There is no opportunity with an MPS to neutralize or rinse away the anti-microbial agent prior to applying the contact lens to the eye.

Generally therefore the art has found it difficult to formulate these MPS solutions to satisfy the following performance criteria. The successful solution must:

1. Show anti-microbial activity to reduce the numbers of common pathogens found on contact lenses to prescribed levels;
2. Show an ability to retard the deposition processes of proteins, lipids, and other materials onto or into the lens and to remove such deposits if they have formed;
3. Be nonirritating to the eye without the help of rinsing and/or neutralizing solutions;
4. Be free of toxic metals or compounds and sensitizing agents so that no long term allergic or toxic response is provoked;
5. Not adversely accumulate within or on the lens or adversely alter the wettability or the parameters (i.e., size, shape, and optical properties) of the lens or be released in amounts toxic to the eye during lens wear;
6. Show adequate shelf-life (e.g. chemical stability);
7. Compatible with enzymes and other agents used in artificial tears or similar accessories to contact lens wear.

A prior art alternative to the use of chemical disinfecting agents are phenolic compounds (e.g., bioflavonoids) as disclosed in De Bruijn International Application PCT/NL97/00092 and Dutch patent NL-1002484. Natural plant derived substances; such as bioflavonoids, can be employed in contact lens care products as natural disinfecting or preserving agents. While the use of bioflavonoids is desirable because they are natural plant products, the majority of bioflavonoids are complex combinations that are difficult to obtain, reproduce and assay.

As background, the method for evaluating the effectiveness of a disinfectant generally requires measuring the ability of the agent to reduce the numbers of viable organisms during a period of time consistent with the normal period of storage of contact lenses between wearings such as six to eight hours, i.e., "overnight". This reduction of numbers of organisms is typically reported in terms of the change in the common log of the microbial population as a result of exposure to the anti-microbial agent. For example, if the agent has effected a reduction in the concentration of a particular organisms in a challenge solution from $10^6$ colony forming units (cfu) per milliliter (ml) to $10^2$ cfu/ml within six hours of exposure then the change, or "log reduction", of the organism as a result of exposure to the agent would be 4.0 (logs). In other words, the number of viable organisms have been reduced to one ten-thousandth of the original level.

In procedures for verifying the effectiveness of contact lens disinfectants generally recognized guidelines call for the use of *Candida albicans* (a yeast), *Fusarium solani* (a mold), *Pseudomonas aeruginosa* (a Gram-negative bacterium), *Staphylococcus aureus* (a Gram-positive bacerium), and *Serratia marcescens* (a Gram-negative bacterium). It is generally accepted in the field of ophthalmic and contact lens solutions that an effective disinfectant will cause at least a three log reduction of each of the bacterial species and a one log reduction of each of the yeast and mold within the storage time advocated for the contact lens care system, typically six to eight hours, i.e., "overnight".

These tests are most often performed by challenging the solution with a concentrated inoculum (e.g., $10^5$–$10^6$ cfu/ml) of each test organism. Over time samples are taken and plated on a growth medium to estimate the number of live organisms remaining at each time point. Of particular interest is the six-hour time point that represents the duration of typical overnight storage of soft contact lenses. It should be apparent that such a challenge represents a worst case scenario since a far greater number of microbes is added than would ever be expected on a contact lens. Further, it should also be apparent that the results of the test may be significantly influenced by other components of the solution besides the disinfectant agent.

In the case of contact lens and ophthalmic solutions various agents are added to enhance compatibility with the eye. To avoid stinging or irritation it is important that the solution possess a tonicity and pH within the physiological range, e.g., 200–350 mOsmole for tonicity and 6.5–8.5 for pH. To this end, various buffering and osmotic agents are often added. The simplest osmotic agent is sodium chloride since this is a major solute in human tears. In addition propylene glycol, lactulose, trehalose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5.

Various viscosity building agents such as polyethylene glycol, surfactants, polyvinylpyrrolidone, polyvinyl alcohol, carboxymethyl cellulose and similar materials may be added to adjust the "body" and "feel" of the solution. Surface active agents, such as polysorbates, polyoxyethylenes and certain phosphonates may be added to ensure proper wetting and/or cleaning. Sequestering agents such as ethylenediaminetetraacetic acid (EDTA), phosphonates, citrate, gluconate and tartarate are also common additives for preservatives of, disinfection or cleaning solutions.

To date, the significant challenge in the development of ophthalmic and contact lens solutions, particularly the MPS solutions, has been to find disinfection agents with sufficient anti-microbial activity that are not at the same time damaging to the eye or contact lens. Due to the complex requirements to keep soft, hydrogel contact lenses clean, free of pathogen microbes, and comfortable to wear without damaging or changing the lens polymer or dimensional parameters and without any harm or side effects to the human eye, only very few compounds or systems have been qualified as suitable ophthalmic or contact lens solutions. It is therefore the object of the present invention to provide a solution that combines the use of a chemical agent (BDT) and natural ingredients with the strength of harsh chemical agents such as hydrogen peroxide while avoiding irritation or damage to the eye.

SUMMARY OF THE INVENTION

The present invention concerns the unexpected discovery that the disinfectant compound, BDT (BenzylDimethyl-[2-

[2-[ (p-1,1,3,3 Tetramethyl butyl) phenoxy)ethoxy]ethyl] amnonium chloride), which has been widely tested and used in hospital surface disinfection, topical pharmaceutical preparations, and even as preservatives for injectables has unexpectedly proven highly effective in the disinfection of contact lenses without irritation to the external ocular surfaces or alteration of the parameters of the contact lens itself. Further, it has been discovered that BDT is stable in aqueous solution and can coexist in an formulation with the variety of cleaning, tonicity, and comfort additives common to ophthalmic and contact lens solutions without an adverse effect on its activity. Finally, it has also been discovered that the effectiveness of ophthalmic solutions containing BDT can be successfully enhanced by the addition of naturally occurring plant products.

The basic active ingredient formulation of the present invention comprises an effective concentration of BDT (preferably 1 to 100 parts per million), either alone or with other additives, in an isotonic or nearly isotonic diluent buffered with an acceptable buffer to the physiologically natural range.

It has been discovered that a variety of discrete, isolated and well-characterized natural plant compounds show anti-microbial and cleaning activity. It has also been discovered that some of these anti-microbial compounds act in a synergistic and or complementary manner with other anti-microbial compounds, such as BDT, and thus enhances their anti-microbial action. The potential range of these anti-microbial compounds includes glycosides, alkaloids, phenolics (anthocyanins, quinones, flavonols and flavonoids, etc.), and terpenoids (including phytosterols and carotenoids). Of particular interest are the following anti-microbial compounds; Allicin, Aucubin, Berberine, Bilberry extract, Caffeic Acid, Chlorogenic Acid, Echinacea extract, Ferulic Acid, Hydrastine, Lipoic Acid, Naringin, Oleuropein, Proanthocyanidins, Quercetin, and Rutin as stand alone disinfection agents or in combination with other anti-microbial agents.

Further, it has been discovered that saponins, can be used as a natural plant surface active or cleaning agents in lens solutions. Specifically triterpenoid saponins and steriod saponins are particularly effective in contact lens or ophthalmic solutions. Also, a wide range of other comfort and cleaning enhancers can be added to the basic solution without adverse affects on the activity of these natural compounds or combinations. Suitable additives include, but are not limited to, various wetting, buffering, osmotic, sequestering, and comfort enhancing agents can be added to enhance the final formulation.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein, specifically to provide an improved contact lens care solution.

The following examples will be employed to demonstrate the effectiveness of BDT as well as its compatibility and being complementary with other desirable additives. In progressing through these examples one can understand the "building blocks" of the preferred embodiment of contact lens and ophthalmic solutions incorporating BDT.

EXAMPLE 1

Initial tests of BDT were made in a contact lens disinfectant solution containing a sodium phosphate buffer system (0.1% anhydrous monobasic sodium phosphate and 0.4% anhydrous dibasic sodium phosphate) made isotonic with sodium chloride (0.7%) and also including Pluronic F127 (0.2%), a polyoxyethylene. Various concentrations of BDT in these vehicles were tested for anti-microbial activity against three of the five organisms that make up the commonly accepted disinfection test panel. The "log reduction" data at six hours after challenge are shown in Table 1. "Log reduction" is the format of data presentation in all of the examples that follow. From these and additional similar experiments it has been observed that increasing concentration of BDT results in increasing kill of a wide range of microbes in six hours or less.

TABLE 1

Effect of BDT Concentration on Microbial Kill

|  | 15 ppm BDT | 25 ppm BDT |
| --- | --- | --- |
| S. aureus | 1.7 | >5.0 |
| P. aeruginosa | 1.8 | 3.4 |
| C. albicans | 0.3 | 1.4 |

EXAMPLE 2

Experiments with a variety of different buffering agents discovered interactions between BDT and the buffer. In particular, a borate-based formula (0.3% boric acid, 0.4% sodium borate, 0.4% sodium chloride and 0.2% Pluronic F127) produced a wider spectrum of microorganism kill than the comparable phosphate-based solution. Especially noteworthy is the enhanced kill of fungus (*Candida albicans*) effected by the use of the borate buffer.

TABLE 2

Comparison of Anti-microbial Activity of BDT in Borate vs. Phosphate Buffer

|  | 25 ppm BDT Borate | 25 ppm BDT Phosphate |
| --- | --- | --- |
| S. aureus | >5.0 | >5.0 |
| P. aeruginosa | >5.0 | 3.4 |
| C. albicans | 4.3 | 1.4 |

EXAMPLE 3

A wide variety of naturally occurring compounds shows anti-microbial activity. In Table 3a results are shown for the enhancement of the kill of *Pseudomonas aeruginosa* using Chlorogenic Acid and Berberine in a phosphate buffered solution with 25 ppm BDT.

TABLE 3a

Enhancement of Pseudomonas kill with Chlorogenic Acid or Berberine

|  | 25 ppm BDT | 25 ppm BDT 500 ppm Chlorogenic Acid | 25 ppm BDT 100 ppm Berberine |
| --- | --- | --- | --- |
| P. aeruginosa | 3.4 | 4.5 | >5.0 |

In Table 3b Caffeic Acid, combined with BDT in the presence of borate buffer, 250 ppm Chlorogenic Acid, and 0.2% Glycerin, improves the kill of *Pseudomonas aeruginosa* while maintaining the excellent log reductions for *Staphylococcus aureus* and *Candida albicans*.

TABLE 3b

Anti-microbial Enhancement of Caffeic Acid to BDT/Chlorogenic Acid

|  | 25 ppm BDT/250 ppm Chlorogenic Acid | 25 ppm BDT/250 ppm Chlorogenic Acid/ 1000 ppm Caffeic Acid |
|---|---|---|
| P. aeruginosa | 2.8 | >5.0 |
| S. aureus | >5.0 | >5.0 |
| C. albicans | >5.0 | 3.8 |

EXAMPLE 4

Table 4 shows the effect of adding 0.2% Glycerin to 25 ppm BDT and 250 ppm chlorogenic acid with borate buffer. In terms of microbiological disinfection this solution is very effective. The addition of Glycerin, a naturally occurring compound has essentially no effect on the disinfectant properties. There is evidence that Glycerin can reduce any minor toxic effects that a disinfectant agent might have on mammalian cells.

TABLE 4

Effect of the Addition of Glycerin on Anti-Microbial Activity

|  | 25 ppm BDT 250 ppm Chlorogenic Acid 0.2% Glycerin | 25 ppm BDT 250 ppm Chlorogenic Acid |
|---|---|---|
| S. aureus | >5.0 | >5.0 |
| P. aeruginosa | 3.9 | 4.4 |
| C. albicans | 3.8 | 4.0 |

EXAMPLE 5

Table 5 shows the effect of adding 0.2% Decanedioic Acid and 0.2% Glycerin to a formulation consisting of 25 ppm BDT and 1000 ppm Caffeic Acid in Borate Buffer. Decanedioic Acid is believed to improve the ocular comfort of contact lens solutions. As show in Table 5, there is no negative impact on anti-microbial activity with both Glycerin and Decanedioic Acid.

TABLE 5

Effect of the Addition of Glycerin + Decanedioic Acid on Anti-Microbial Activity

|  | 25 ppm BDT 1000 ppm Caffeic Acid | 25 ppm BDT 1000 ppm Caffeic Acid 0.2% Glycerin 0.2% Decanedioic Acid |
|---|---|---|
| S. aureus | >5.0 | >5.0 |
| P. aeruginosa | >5.0 | >5.0 |
| C. albicans | 3.3 | >5.0 |

EXAMPLE 6

When the solutions were tested on animals, there was no observed toxicity or irritation when the materials were used in a "normal wear" cycle. That is, an isotonic BDT solution at physiological pH was tested on rabbits using Wohlk Weflex lenses. The lenses were disinfected in the test solution or in a control solution overnight. The lenses were then applied to the animals and worn by the animals for 8 hours of every 24 hours. This cycle was repeated for 21 days with no signs of irritation or toxicity. A second study used SUREVUE™ contact lenses. The lenses were soaked in the test solutions for 12 hours and then applied to the eyes of animals for a 12 hour wear cycle. Then a freshly soaked lens was substituted. This exaggerated wear test was on for 14 days of continuous wear of the test period. At the end examination of the animal eyes showed no signs of irritation or toxicity. Equivalent results were noted for the control solution, which was a commercially marketed MPS.

EXAMPLE 7

A clinical study was conducted over a three month period with seven patients wearing SUREVUE™(n=6) and Medalist™ (n=1) contact lenses. Patients received new lenses at the beginning of the study. The lenses were soaked overnight in an isotonic BDT test solution at physiological pH and rinsed in saline prior to wear. After 21 days there were no significant slit lamp findings, no irritation of the conjunctiva and no lens deposits reported. No irritation or other negative findings were found during the tenure of the study.

EXAMPLE 8

Table 8-a shows the anti-microbial activity of two naturally-occurring compounds, caffeic acid and chlorogenic acid, at 1000 ppm in borate-buffered saline. The borate-buffered saline alone was used as a control. It is evident that both naturally-occurring compounds have substantial anti-microbial activity against *Pseudomonas aeruginosa* within the six-hour challenge period. Either compound therefore may be useful as a preservative or disinfectant agent in a ophthalmic solutions.

TABLE 8-a

Anti-Microbial Activity of Caffeic Acid and Chlorogenic Acid in Borate-Buffered Saline

|  | Borate-Buffered Saline | 1000 ppm Caffeic Acid | 1000 ppm Chlorogenic Acid |
|---|---|---|---|
| S. aureus | 0 | 0.7 | 0.4 |
| P. aeruginosa | 0 | >5.0 | 2.2 |
| C. albicans | 0 | 0.2 | 0.1 |

Table 8-b shows the anti-microbial activity of a third naturally-occurring compound, berberine, at concentrations of 25 and 100 ppm in phosphate-buffered saline. It is evident that 100 ppm berberine has anti-microbial activity against *Pseudomonas aeruginosa* and *Staphylococcus aureus* within the 6-hour challenge period. Berberine may therefore be useful as a preservative or disinfectant agent in a ophthalmic solutions.

TABLE 8-b

Anti-Microbial Activity of Berberine at Two Concentrations in Phosphate-Buffered Saline

|  | 25 ppm Berberine | 100 ppm Berberine |
|---|---|---|
| S. aureus | 0 | 1.5 |
| P. aeruginosa | 0.1 | 1.8 |
| C. albicans | 0 | 0 |

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

We claim:

1. A contact lens solution containing a microbicidal concentration of Benzyldimethyl {2-[2-(p-1,1,3,3-tetramethylbutylphenoxy) ethoxy]ethyl} ammonium chloride.

2. The contact lens solution of claim 1, wherein the concentration of Benzyldimethyl {2-[2-(p-1,1,3,3-tetramethylbutylphenoxy) ethoxy]ethyl} ammonium chloride is between 1 and 100 parts per million.

3. The contact lens solution of claim 1, further comprising a physiologically compatible buffer selected from the group consisting of phosphate, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

4. The contact lens solution of claim 1, further comprising a osmotic agent selected from the group consisting of trehalose, mannitol, sorbitol, lactulose, sodium chloride, andpropylene glycol.

5. The contact lens solution of claim 1, further comprising between 0.01% and 5.0% glycerin.

6. The contact lens solution of claim 1 further comprising between 0.01% and 2.0% of decanedioic acid.

7. The contact lens solutions of claim 1 further comprising between 10 and 2500 parts per million of allantoin.

8. The contact lens solution of claim 1 further comprising a wetting agent selected from the group consisting of polysorbate surfactants, polyoxyethylene surfactants, phosphonates, and saponins.

9. The contact lens solution of claim 1 further comprising a sequestering agent selected from the group consisting as ethylenediaminetetraacetic acid, phosphonates, citrate, gluconate and tartarate.

10. The contact lens solution of claim 1 further comprising a naturally-occurring compound as an additional microbicidal agent and selected from the group consisting of allicin, aucubin, berberine, bilberry extract, caffeic acid, chlorogenic acid, echinacea extract, ferulic acid, hydrastine, lipoic acid, naringin, oleuropein, proanthocyanidins, quercetin, and rutin.

11. The contact lens solution of claim 1 further comprising a viscosity altering agent.

12. The contact lens solution of claim 11, wherein the viscosity altering agent is selected from the group consisting of polyvinylpyrrolidone, polyethylene glycol, polyvinyl alcohol, cellulose polymers and mixtures thereof.

13. A hydrogen peroxide-free ophthalmic solution comprised of between 10 and 10,000 parts per million of a naturally-occurring microbicidal compound selected from the group consisting of allicin, aucubin, berberine, bilberry extract, caffeic acid, chlorogenic acid, echinacea extract, ferulic acid, hydrastine, lipoic acid, naringin, oleuropein, proanthocyanidins, quercetin, and rutin.

14. The ophthalmic solution of claim 13 further comprising a viscosity altering agent.

15. The ophthalmic solution of claim 13 further comprising a sequestering agent.

16. The ophthalmic solution of claim 13 further comprising a wetting agent.

17. The ophthalmic solution of claim 16, wherein the wetting agent comprising a saponin.

18. The ophthalmic solution of claim 13 further comprising an osmotic agent.

19. A contact lens solution comprising: between 1 and 100 parts per million Benzyldimethyl {2-[2-(p-1,1,3,3-tetramethylbutylphenoxy) ethoxy]ethyl} ammonium chloride, between 10 and 10000 parts per million of a naturally-occurring plant product, and borate buffer.

20. The contact lens solution of claim 19 further comprising an osmotic agent selected from the group consisting of trehalose, mannitol, sorbitol, lactulose, sodium chloride, and propylene glycol.

21. The contact lens solution of claim 19 further comprising between 0.01% and 2.0% glycerin.

22. The contact lens solution of claim 19 further comprising between 0.01% and 2.0% of decanedioic acid.

23. The contact lens solutions of claim 19 further comprising between 10 and 2500 parts per million of allantoin.

24. The contact lens solution of claim 19 further comprising a wetting agent selected from the group consisting of polysorbate surfactants, polyoxyethylene surfactants, phosphonates, and saponins.

25. The contact lens solution of claim 19 further comprising a sequestering agent selected from the group consisting as ethylenediaminetetraacetic acid, phosphonates, citrate, gluconate and tartarate.

26. The contact lens solution of claim 19 wherein the naturally-occurring plant product is selected from the group consisting of allicin, aucubin, berberine, bilberry extract, caffeic acid, chlorogenic acid, echinacea extract, ferulic acid, hydrastine, lipoic acid, naringin, oleuropein, proanthocyanidins, quercetin, and rutin.

27. The contact lens solution of claim 19 further comprising a viscosity altering agent.

28. The contact lens solution of claim 27, wherein the viscosity altering agent is selected from the group consisting of polyvinylpyrrolidone, polyethylene glycol, polyvinyl alcohol, and cellulose polymer.

29. A contact lens solution comprising: between 10 and 50 parts per million Benzyldimethyl {2-[2-(p-1,1,3,3-tetramethylbutylphenoxy) ethoxy]ethyl} ammonium chloride, between 100 and 2000 parts per million of caffeic acid and a borate buffer.

30. The contact lens solution of claim 29 further comprising an osmotic agent selected from the group consisting of trehalose, mannitol, sorbitol, lactulose, sodium chloride, and propylene glycol.

31. The contact lens solution of claim 29 further comprising between 0.01% and 2.0% glycerin.

32. The contact lens solution of claim 29 further comprising between 0.01% and 2.0% of decanedioic acid.

33. The contact lens solutions of claim 29 further comprising between 10 and 2500 parts per million of allantoin.

34. The contact lens solution of claim 29 further comprising a wetting agent selected from the group consisting of polysorbate surfactants, polyoxyethylene surfactants, phosphonates, saponins and mixtures thereof.

35. The contact lens solution of claim 29 further comprising a sequestering agent selected from the group consisting as ethylenediaminetetraacetic acid, phosphonates, citrate, gluconate and tartarate.

36. The contact lens solution of claim 29 further comprising a viscosity altering agent selected from the group consisting of polyvinylpyrrolidone, polyethylene glycol, polyvinyl alcohol, and cellulose polymers.

37. A contact lens cleaning solution comprising between 0.01% and 2.5% saponins as cleaning agents.

38. A contact lens cleaning solution comprising a naturally-occurring microbicidal compound selected from the group consisting of berberine, caffeic acid, and chlorogenic acid, and a borate buffer.

39. A method for cleaning and disinfecting contact lenses comprising the steps of:

contacting a contact lens to be cleaned and disinfected with an aqueous solution of between 1 and 100 parts per million of Benzyldimethyl {2-[2-(p-1,1,3,3-tetramethylbutylphenoxy) ethoxy]ethyl} ammonium chloride;

leaving the lens in contact with said aqueous solution for a predetermined time; and removing the lens from said solution and placing it onto a user's eye without rinsing.

40. The method of claim 39, wherein said aqueous solution further comprises a physiologically compatible buffer selected from the group consisting of phosphate, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

41. The method of claim 39, wherein said aqueous solution further comprises a naturally-occurring plant product as an additional microbicidal agent and selected from the group consisting of allicin, aucubin, berberine, bilberry extract, caffeic acid, chlorogenic acid, echinacea extract, ferulic acid, hydrastine, lipoic acid, naringin, oleuropein, proanthocyanidins, quercetin, and rutin.

42. The method of claim 39 wherein the contact lens is selected from the group consisting of rigid gas permeable contact lenses and soft contact lenses.

43. A method for cleaning and disinfecting contact lenses comprising the steps of:

contacting a contact lens to be cleaned and disinfected with hydrogen peroxide-free aqueous solution of between 10 and 10,000 parts per million of a naturally-occurring microbicidal compound selected from the group consisting of allicin, aucubin, berberine, bilberry extract, caffeic acid, chlorogenic acid, echinacea extract, ferulic acid, hydrastine, lipoic acid, naringin, oleuropein, proanthocyanidins, quercetin, and rutin;

leaving the lens in contact with said aqueous solution for a predetermined time; and removing the lens from said solution and placing it onto a user's eye without rinsing.

44. The method of claim 43, wherein said aqueous solution further comprises a physiologically compatible buffer selected from the group consisting of phosphate, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

45. The method of claim 43, wherein said aqueous solution further comprises between wherein the concentration of Benzyldimethyl {2-[2-(p-1,1,3,3-tetramethylbutylphenoxy) ethoxy]ethyl} ammnonium chloride is between 1 and 100 parts per million.

46. The method of claim 43 wherein the contact lens is selected from the group consisting of rigid gas permeable contact lenses and soft contact lenses.

47. An ophthalmic solution comprising between 10 and 10,000 parts per million of a naturally-occurring microbicidal compound selected from the group consisting of allantoin, allicin, aucubin, berberine, bilberry extract, caffeic acid, chlorogenic acid, echinacea extract, ferulic acid, hydrastine, lipoic acid, naringin, oleuropein, proanthocyanidins, quercetin, and rutin, and further comprising a saponin as a wetting agent.

* * * * *

UNITED STATES PATENT AND TRADEMARK OFFICE
CERTIFICATE OF CORRRECTION

PATENT N: 6,162,393
DATED : December 19, 2000
INVENTOR: Chris De Bruiju, et al.

It is certified that error appears in the above-identified patent and that said Letters Patent is hereby corrected as shown below:

On the title page, item [56] insert the following:

| | | DOCUMENT NUMBER | | | | | | PUBLICATION DATE | COUNTRY OR PATENT OFFICE | CLASS | SUBCLASS | TRANSLATION | |
|---|---|---|---|---|---|---|---|---|---|---|---|---|---|
| | | | | | | | | | | | | YES | NO |
| | | 1 | 0 | 0 | 2 | 4 | 8 | 4 | Nov. 3, 1997 | The Netherlands | | | |

Signed and Sealed this

Twenty-seventh Day of March, 2001

Attest:

NICHOLAS P. GODICI

Attesting Officer

Acting Director of the United States Patent and Trademark Office